United States Patent
Mitrofanov

(10) Patent No.: US 7,608,827 B2
(45) Date of Patent: Oct. 27, 2009

(54) NEAR-FIELD TERAHERTZ IMAGING

(75) Inventor: Oleg Mitrofanov, New York, NY (US)

(73) Assignee: Alcatel-Lucent USA Inc., Murray Hill, NJ (US)

( * ) Notice: Subject to any disclaimer, the term of this patent is extended or adjusted under 35 U.S.C. 154(b) by 387 days.

(21) Appl. No.: 11/350,992

(22) Filed: Feb. 9, 2006

(65) Prior Publication Data

US 2007/0181811 A1   Aug. 9, 2007

(51) Int. Cl.
*G01J 4/04* (2006.01)

(52) U.S. Cl. ............ 250/358.1; 359/247; 359/346

(58) Field of Classification Search ............ 250/341.1, 250/358.1; 359/247, 346
See application file for complete search history.

(56) References Cited

U.S. PATENT DOCUMENTS

| | | | |
|---|---|---|---|
| 5,623,145 A | 4/1997 | Nuss | 250/330 |
| 5,710,430 A | 1/1998 | Nuss | 250/358.1 |
| 5,789,750 A | 8/1998 | Nuss | 250/338.1 |
| 5,894,125 A | 4/1999 | Brener et al. | 250/330 |
| 5,939,721 A | 8/1999 | Jacobsen et al. | 250/330 |
| 6,078,047 A | 6/2000 | Mittleman et al. | 250/338.1 |
| 6,690,873 B2 * | 2/2004 | Bendett et al. | 385/132 |
| 7,205,941 B2 * | 4/2007 | Wang et al. | 343/700 MS |
| 7,336,062 B2 * | 2/2008 | Mitrofanov | 324/96 |
| 7,405,866 B2 * | 7/2008 | Kuekes et al. | 359/321 |
| 2005/0018276 A1 * | 1/2005 | Kourogi et al. | 359/333 |
| 2005/0230625 A1 * | 10/2005 | Zhang et al. | 250/341.1 |
| 2006/0238866 A1 * | 10/2006 | Von Lerber | 359/487 |
| 2006/0255277 A1 * | 11/2006 | Cole et al. | 250/341.1 |

FOREIGN PATENT DOCUMENTS

WO   WO 03/023383 A2 *   3/2003

OTHER PUBLICATIONS

U.S. Appl. No. 10/983,864, filed Nov. 8, 2004, Mitrofanov.
"Laser Excess Noise Reduction in Optical Phase-Shift Measurements," by O. Mitrofanov, Applied Optics, 2003, vol. 42, pp. 2526-2531.

* cited by examiner

*Primary Examiner*—David P Porta
*Assistant Examiner*—David S Baker
(74) *Attorney, Agent, or Firm*—Mendelsohn, Drucker & Associates, P.C.

(57) ABSTRACT

A T-ray imaging system employing an optical resonator that is adapted to be (i) positioned in the near-field proximity to a surface of a sample and (ii) pumped with pump light such that the pump light traverses a relatively thin layer of an electro-optically responsive material (EORM) located in the resonator's cavity. The imaging system has an optical detector that is adapted to detect at least a portion of the pump light reflected from the resonator, while the sample is illuminated with terahertz (THz) radiation such that the EORM is exposed to that radiation resulting in a detectable phase shift in the reflected pump light.

22 Claims, 4 Drawing Sheets

NEAR-FIELD TERAHERTZ IMAGING

CROSS-REFERENCE TO RELATED APPLICATIONS

The subject matter of this application is related to that of U.S. patent application Ser. No. 10/983,864, filed on Nov. 8, 2004, and entitled "Optically Measuring Electric Field Intensities," which is incorporated herein by reference in its entirety.

BACKGROUND OF THE INVENTION

1. Field of the Invention

The present invention relates to imaging various media or objects using scattered, reflected, and/or transmitted radiation in the terahertz (THz) region of the electromagnetic spectrum and, more particularly, to optical detection of THz radiation.

2. Description of the Related Art

The term "terahertz radiation" refers herein to electromagnetic radiation having wavelengths in a range between about 10 μm and about 10 mm. Terahertz (THz) radiation can penetrate well most nonmetallic objects, such as paper, cardboard, plastics, and moderate thickness of many dielectrics, while being blocked or absorbed by metals and polar materials. As a result, the THz spectral range is becoming increasingly important for such applications as remote sensing of gases, quality control of plastic and composite materials, package inspection, moisture analysis, etc. A relatively recent development is the use of THz radiation for imaging, often referred to as T-ray imaging. Description of representative prior-art T-ray imaging systems can be found, e.g., in commonly owned U.S. Pat. Nos. 5,623,145, 5,710,430, 5,894,125, and 6,078,047, the teachings of all of which are incorporated herein by reference.

One problem with T-ray imaging is that the wavelength ($\lambda$) of THz radiation is relatively large compared to, e.g., that of visible light. As a result, the spatial resolution of T-ray images is generally relatively poor, because the spatial resolution is typically related to the wavelength of the interrogating radiation. To address this problem, near-field T-ray imaging techniques have been proposed. In near-field T-ray imaging, the spatial resolution is generally limited not by the value of $\lambda$, but by the effective aperture of the imaging apparatus. When an apparatus having a relatively small effective aperture is configured to scan an object illuminated by THz radiation, a T-ray image of the object having a relatively high spatial resolution, e.g., better than the applicable T-ray diffraction limit (i.e., $\sim\lambda/2$), can be created.

One convenient method of detecting THz radiation is based on an electro-optic (EO) effect. More specifically, an EO effect causes the refractive index of an electro-optically responsive material to depend on the intensity of an electric field, e.g., that of THz radiation. As a result, light traveling through the electro-optically responsive material acquires a phase retardation related to the light propagation distance and the intensity of the THz field. The latter can therefore be deduced by pumping the electro-optically responsive material with pump light and measuring the pump-light phase retardation.

The use of EO detection in near-field T-ray imaging has however encountered difficulties because, for near-field imaging, a relatively small EO interaction region is used to substantially avoid the near-field to far-field conversion of the THz radiation inside the EO detector. Unfortunately, the relatively small EO interaction region generally causes the phase retardation acquired by the pump light in that region to also be relatively small, which hampers an accurate intensity determination of the THz field.

SUMMARY OF THE INVENTION

Problems in the prior art are addressed by various embodiments of a T-ray imaging system employing an optical resonator that is adapted to be (i) positioned in a near-field proximity to a surface of a sample to be imaged and (ii) pumped with pump light such that the pump light traverses a relatively thin layer of an electro-optically responsive material (EORM) located in the resonator's cavity. The imaging system has an optical detector that is adapted to detect at least a portion of the pump light reflected from the resonator, while the sample is illuminated with terahertz (THz) radiation such that the EORM is exposed to that radiation resulting in a detectable phase shift in the reflected pump light.

Advantageously, an imaging system of the invention is capable of providing a relatively high sensitivity, while utilizing a relatively small electro-optic (EO) probe that is suitable for near-field imaging. More specifically, an optical resonator incorporated into the EO probe causes the pump light to traverse the resonator's EORM layer multiple times, thereby causing the phase retardation induced in the pump light within the EORM layer due to the presence of the THz electric field to accumulate. Due to this accumulation, an imaging system of the invention is capable of providing a sensitivity that is significantly higher than the sensitivity obtained with a conventional (i.e., having no resonator) EO probe of a similar size. In addition, in certain embodiments, an imaging system of the invention can be configured to perform an optical-beam scan of the sample, while the sample, the EO probe, the pump-light source, the T-ray source, and the optical detector remain stationary, or to have projection optics and a two-dimensional image sensor, onto which the pump beam reflected from the EO probe is projected to form a T-ray image of the sample.

According to one embodiment, the present invention is a method of detecting interrogation radiation, comprising: pumping an optical resonator having an EORM with pump light, wherein the pump light traverses the EORM; and detecting at least a portion of the pump light output from the resonator, while exposing the EORM to the interrogation radiation.

According to another embodiment, the present invention is a system, comprising: an optical resonator having an EORM, wherein said resonator is adapted to be pumped with pump light such that the pump light traverses the EORM, wherein the EORM is adapted to be exposed to interrogation radiation; and an optical detector adapted to detect at least a portion of the pump light output from the resonator having the EORM exposed to the interrogation radiation.

BRIEF DESCRIPTION OF THE DRAWINGS

Other aspects, features, and benefits of the present invention will become more fully apparent from the following detailed description, the appended claims, and the accompanying drawings in which:

DETAILED DESCRIPTION

Figure 1:
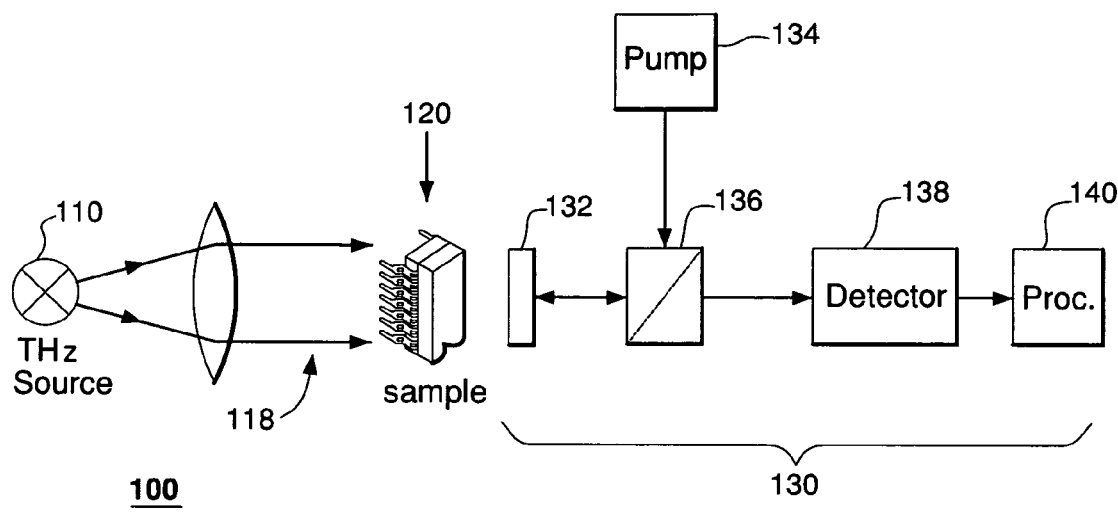
FIG. 1 shows a block diagram of a T-ray imaging system according to one embodiment of the invention.

FIG. 1 shows a block diagram of an imaging system 100 according to one embodiment of the invention. System 100 has (i) a THz-radiation source 110 configured to illuminate a sample 120 and (ii) a detection subsystem 130 configured to measure the THz-radiation field in close proximity to the sample to produce a T-ray image of the sample. Illustratively, system 100 is shown in a transmission configuration, in which a collimated beam 118 of THz radiation originating at source 110 passes through sample 120 before being measured by detection subsystem 130. One skilled in the art will appreciate that other system configurations are also possible. For example, in a scattering configuration (not shown) of system 100, the relative positions of source 110, sample 120, and detection subsystem 130 are such that, rather than detecting a beam of T-rays directly transmitted through the sample, as in the transmission configuration shown in FIG. 1, the detection subsystem is configured to detect the T-rays scattered and/or reflected by the sample.

Detection subsystem 130 is designed to measure the THz-radiation field based on an electro-optic (EO) effect and includes an EO probe 132, an optical pump 134, a beam splitter 136, an optical detector 138, and a signal processor 140. Optical pump 134 generates an optical pump beam, at least a portion of which is directed by beam splitter 136 toward EO probe 132. The pump beam traverses EO probe 132 and is reflected back toward beam splitter 136, which further directs at least a portion of the reflected beam to optical detector 138. EO probe 132 has a layer of an electro-optically responsive material (EORM), which is traversed by the pump beam. Due to the presence of the THz-radiation field produced by beam 118, the EORM layer causes the pump light to acquire a phase retardation having a magnitude related to the intensity of the THz-radiation field in the EORM layer. Detector 138 receives the phase-retarded pump light from EO probe 132 and converts it into an electrical signal indicative of the phase-retardation value. The signal produced by detector 138 is then applied to signal processor 140, where that signal is processed to obtain the intensity of the THz radiation field in the EORM layer.

EO probe 132 is designed such that its EORM layer can be placed in near-field proximity to, e.g., a few microns from, the surface of sample 120. Thus, when EO probe 132 is so placed, detection subsystem 130 becomes configured to measure the near-field intensity of the THz radiation at the surface of sample 120. The volume in which the near-field intensity of the THz radiation is probed by detection subsystem 130 (the "probed volume") is determined by the lateral size of the optical pump beam in the EORM layer of EO probe 132 and by the thickness of that layer. The minimum lateral size of the pump beam achievable by focusing that beam is generally limited by the diffraction limit of the pump light. As will be clear from the description below, the thickness of the EORM layer can be as small as about one half of the pump-light wavelength. Consequently, if system 100 is configured to use pump light having a wavelength of 980 nm, then the probed volume can be as small as about 0.1 $\mu m^3$ and the system is capable of mapping the near-field intensity of the THz radiation at the surface of sample 120 with the corresponding, relatively high spatial resolution.

In one embodiment, system 100 has a translation stage (not shown) adapted to move sample 120 with respect to source 110 and detection subsystem 130, which remain stationary. The sample translation enables system 100 to map the intensity of THz radiation in the near-field proximity to sample 120, thereby generating a near-field T-ray image of the sample. In another embodiment, system 110 has a translation stage (not shown) adapted to move detection subsystem 130, or an appropriate part thereof, with respect to source 110 and sample 120, which remain stationary. Such detection-subsystem translation similarly enables system 100 to generate a near-field T-ray image of the sample. In yet another embodiment, detection subsystem 130 is configured to perform a two-dimensional scan of the pump beam over the surface of probe 132, while source 110, sample 120, and the EO probe itself remain stationary. If EO probe 132 has an appropriate size and geometry, then the optical pump-beam scanning also enables system 100 to generate a near-field T-ray image of the sample. In still another embodiment, optical detector 138 incorporates projection optics and a two-dimensional image sensor, onto which the pump beam reflected from EO probe 132 is projected to form a T-ray image of sample 120.

In various configurations, system 100 can use CW and/or pulsed electromagnetic radiation in its operation. For example, in one configuration, both THz-radiation source 110 and optical pump 134 produce respective CW beams. In another configuration, one of THz-radiation source 110 and optical pump 134 produces a CW beam, while the other produces a pulsed beam. In yet another configuration, both THz-radiation source 110 and optical pump 134 produce pulsed beams. The pulses forming these beams are synchronized such that a THz-radiation pulse and a corresponding pump-light pulse arrive at the EORM layer of EO probe 132 at substantially the same time.

Figure 2:
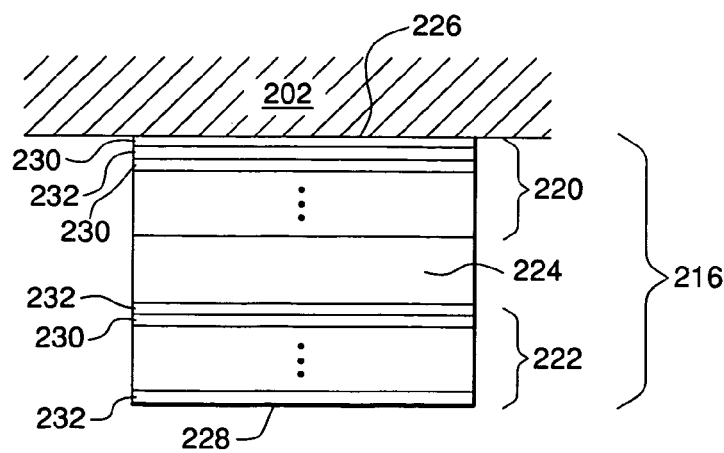
FIG. 2 shows a side cross-sectional view of an electro-optic (EO) probe that can be used in the imaging system of FIG. 1 according to one embodiment of the invention.

FIG. 2 shows a side cross-sectional view of an EO probe 200 that can be used as EO probe 132 in system 100 according to one embodiment of the invention. EO probe 200 is generally analogous to an EO probe described in the above-cited U.S. patent application Ser. No. 10/983,864. EO probe 200 has an increased sensitivity compared to that of a conventional EO probe because EO probe 200 incorporates an optical resonator having an EORM layer located inside the resonator's cavity. Due to the presence of the resonator, the EORM layer is traversed by the pump light multiple times, which enables the phase retardation induced in the EORM layer by the presence of an external, e.g., THz, electric field to accumulate. As a result, EO probe 200 provides relatively high sensitivity, while having relatively small linear dimensions suitable for near-field imaging.

In one embodiment, EO probe 200 includes an optical resonator 216 mounted on an optically transparent substrate 202. Substrate 202 is adapted to provide mechanical strength to generally thin and, thus, relatively structurally weak resonator 216. In addition, substrate 202 can conveniently be used to form optical resonator 216 on the substrate using, e.g., molecular-beam epitaxy. Optical resonator 216 includes: (i) top and bottom reflectors 220, 222 that define the optical resonator's cavity and (ii) an EORM layer 224 interposed between reflectors 220 and 222. Top reflector 220 has a lower reflectivity than bottom reflector 222 so that the pump light, e.g., from optical pump 134 (see FIG. 1), can enter and leave the resonator's cavity via substrate 202 and a top surface 226 of optical resonator 216. Bottom reflector 222 has a relatively high reflectivity so that little or no pump light can leak through a bottom surface 228 of optical resonator 216, e.g., to fall onto sample 120 (see FIG. 1). The materials used in EO probe 200 are generally chosen such that the probe is generally transparent to THz radiation.

Each of reflectors 220 and 222 is a distributed Bragg reflector formed by one or more pairs of alternating layers 230 and 232. Layers 230 and 232 have different refractive indices, and each of these layers has a thickness substantially equal to one quarter of the wavelength of the pump light in the layer. EORM layer 224 has a thickness substantially equal to a positive integer multiple of one half of the wavelength of the pump light therein. In a representative embodiment, top reflector 220 has fewer pairs of layers 230 and 232 than does bottom reflector 222. As a result, top reflector 220 has a lower reflectivity than that of bottom reflector 222, which enables (i) EORM layer 224 to be pumped with pump light through top surface 226, (ii) the phase-retarded pump beam to leave the resonator's cavity via the top surface after several reverberations inside the cavity, and (iii) bottom reflector 222 to substantially block the pump light from leaking through bottom surface 228. In one embodiment, each layer 230 is a GaAs layer, each layer 232 is an $Al_xGa_{(1-x)}As$ layer, and EORM layer 224 is a monocrystalline GaAs layer, with the plane of the EORM layer being parallel to the (100) crystal plane of the GaAs for probing THz radiation with the electric-field vector polarized in the direction perpendicular to that crystal plane. In another embodiment, EORM layer 224 is a monocrystalline GaAs layer, with the plane of the EORM layer being parallel to the (110) crystal plane of the GaAs for probing THz radiation with the electric-field vector polarized in the direction parallel to that crystal plane.

Figure 3:
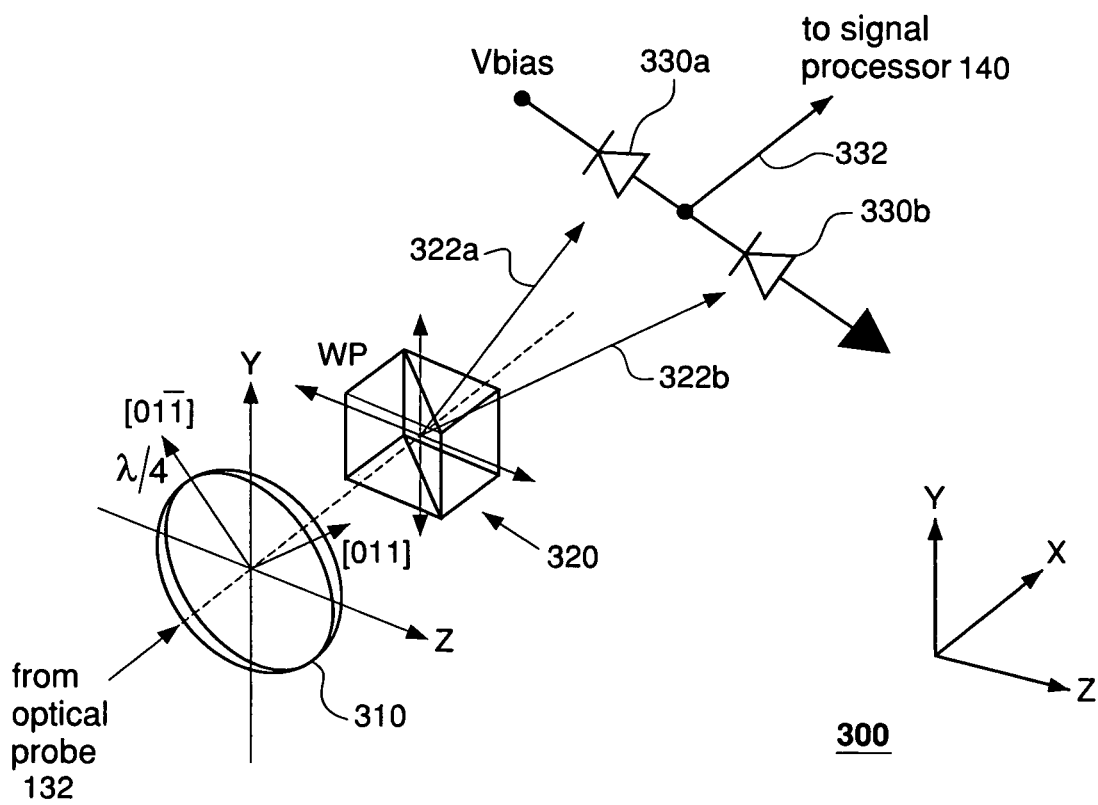
FIG. 3 schematically shows an optical detector that can be used in the system of FIG. 1 according to one embodiment of the invention.

FIG. 3 schematically shows an optical detector 300 that can be used as optical detector 138 in system 100 according to one embodiment of the invention. In a typical configuration of detection subsystem 130, the pump beam impinging upon EO probe 132 is polarized at 45 degrees with respect to the principal axes of the EORM layer of the EO probe. As a result, in the EORM layer of EO probe 132, the probe beam propagates as two orthogonal principal-axis polarizations of equal intensities, and a phase shift (retardation, δ) between these principal-axis polarizations is accumulated due to the presence of the THz-radiation field produced by source 110. For example, for a (100)-oriented GaAs EORM layer 224, the pump beam propagates along the [100] direction and is polarized along the Y axis (see FIG. 3), and the principal axes are the [011] and [011] axes.

Detector 300 has a Wollaston prism (WP) 320 configured as a polarizing beam splitter that adds (i.e., constructively interferes) and subtracts (i.e., destructively interferes) the two principal-axis polarizations to form two optical beams 322a-b, respectively. In the absence of a quarter-wave plate 310, the intensities of beams 322a-b depend on the value of δ as $\sin^2$ (δ/2) and $\cos^2$ (δ/2), respectively, which dependence can be easily derived by one skilled in the art, e.g., using the Jones-matrix calculus. Quarter-wave plate 310, which is placed in detector 300 in front of WP 320, serves to shift the operating point of the detector by 90 degrees. More specifically, the orientation of the optical axes of quarter-wave plate 310 substantially coincides with the orientation of the principal axes of the EORM layer of EO probe 132, which inserts a constant π/2 phase shift between the principal-axis polarization components as described by Eqs. (1A-B):

$$I_{322a} = I_0 \sin^2\left(\frac{\pi}{4} + \frac{\delta}{2}\right) \quad (1A)$$

$$I_{322b} = I_0 \cos^2\left(\frac{\pi}{4} + \frac{\delta}{2}\right) \quad (1B)$$

where $I_{322a}$ and $I_{322b}$ are the intensities of output beams 322a-b, respectively, and $I_0$ is the intensity of the pump beam.

Detector 300 further includes a balanced pair of photodetectors 330a-b that are configured to receive optical beams 322a-b, respectively, and convert them into the corresponding electrical signals. Since photodetectors 330a-b are serially connected as indicated in FIG. 3, an output signal 332 produced by optical detector 300 (and then applied to, e.g., signal processor 140, FIG. 1) is substantially a difference signal described by Eq. (2):

$$S_{332} = k(I_{330a} - I_{330b}) \quad (2)$$

where $S_{332}$ is the magnitude of signal 332 and k is the conversion coefficient of photodetectors 330a-b. Eqs. (1-2) can be expanded into a Taylor expansion series and, at small values of δ, signal 332 becomes substantially proportional to δ. As a result, signal 332 can be converted by processor 140 into the corresponding electric-field values in a relatively straightforward manner. More details on various embodiments of detector 300 and its physical principle of operation can be found, e.g., in the above-cited U.S. patent application Ser. No. 10/983,864 and in an article by O. Mitrofanov published in Applied Optics, 2003, vol. 42, pp. 2526-31, and entitled "Laser Excess Noise Reduction in Optical Phase-Shift Measurements," which article is incorporated herein by reference.

Figure 4A:
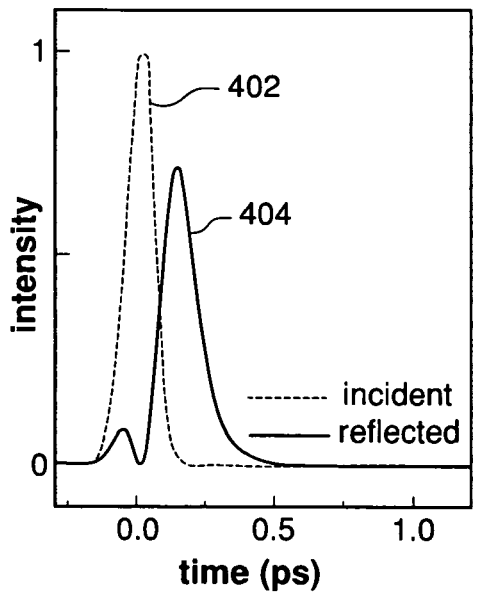
FIGS. 4A-B graphically illustrate certain signals produced in one embodiment of the detection subsystem of the imaging system of FIG. 1.
Figure 4B:
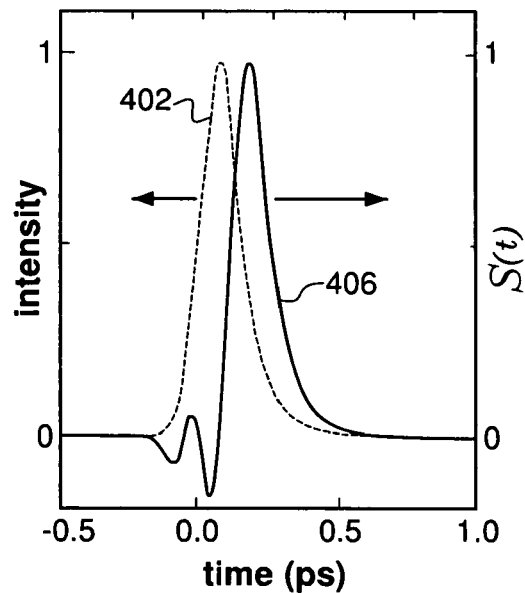

FIGS. 4A-B graphically illustrate certain signals produced in one embodiment of detection subsystem 130. More specifically, in the embodiment illustrated by FIG. 4: (I) optical pump 134 is adapted to generate pulsed pump light having a wavelength ($\lambda_0$) of 980 nm and a pulse duration of about 100 fs; (II) EO probe 132 is EO probe 200 (FIG. 2) having optical resonator 216 that is about 4 μm thick, wherein (a) EORM layer 224 is made of GaAs and has a thickness D=$\lambda_0$/2n, where n is the refractive index of GaAs, and (b) Bragg reflectors 220 and 222 are composed of GaAs and $Al_{0.9}Ga_{0.1}As$ quarter-wavelength layer pairs and have five and sixteen such layer pairs, respectively; and (III) optical detector 138 is optical detector 300 (FIG. 3). FIG. 4A shows the intensity of an optical signal incident upon EO probe 132 (dashed-line waveform 402) and a corresponding optical signal reflected from the EO probe (solid-line waveform 404); and FIG. 4B shows the resulting signal 332 (solid-line waveform 406) generated by photodetectors 330a-b (see FIG. 3), with waveform 402 (FIG. 4A) shown again in FIG. 4B as a reference. The horizontal axes in FIGS. 4A-B corresponds to a (real) time window that includes a single pump pulse.

Referring to FIG. 4A, waveform 404 has two peaks, a relatively small first peak centered near 0.0 ps and a relatively large second peak centered at about 0.2 ps. The first peak appears in the reflected light before the pump light corresponding to waveform 402 has reached EORM layer 224 of EO probe 200 and is produced by the direct pump-light reflection from reflector 220. As the pump light reaches EORM layer 224 and the light intensity inside optical resonator 216 builds up during the duration of the pump pulse, the light leaking out of the resonator's cavity through reflector 220 starts to interfere destructively with the pump light that is reflected directly from that reflector without penetrating into the resonator's cavity. Hence, the magnitude of waveform 404 decreases, thereby resulting in the formation of the first peak. The destructive interference lasts only until about the end of the incident pump pulse, after which time the magnitude of waveform 404 begins to rise again, thereby leading to the formation of the second peak. This second peak in waveform 404 originates substantially entirely from the light that exits the resonator's cavity after several reverberations inside the cavity.

Referring to FIG. 4B, waveform 406 represents signal 332 (FIG. 3) if photodetectors 330a-b have a sufficiently fast response time commensurate with the time scale of temporal variations in waveform 404 (FIG. 4A). If optical detector 300 is configured with relatively slow photodetectors 330a-b, then signal 332 produced by that optical detector will substantially correspond to an integral of waveform 406.

As already explained above, the presence of a THz-radiation field in EORM layer 224 causes the pump light reflected from EO probe 200 to be phase retarded. Since the phase retardation acquired by a photon depends on the time interval that the photon remains in the resonator's cavity, the phase-retardation value tends to increase toward the end of the second peak in waveform 404. As such, the information about phase-retardation in EORM layer 224 and, thus, the THz-radiation field intensity can be obtained from the relatively large peak of waveform 406 that corresponds to the second peak in waveform 404. In contrast, the relatively fast transient oscillation in waveform 406 that precedes the relatively large peak corresponds to the first peak in waveform 404 and, as such, is mostly indicative of the electro-optic phase shift acquired within the alternate layer structure of reflector 220, rather than that within EORM layer 224. As a result, the use of optical detector 300 configured with relatively slow photodetectors 330a-b might in fact be beneficial because the integration of the fast transient oscillation in waveform 406 will average out that oscillation and substantially cancel its contribution to the measured magnitude of signal 332.

Figure 5:
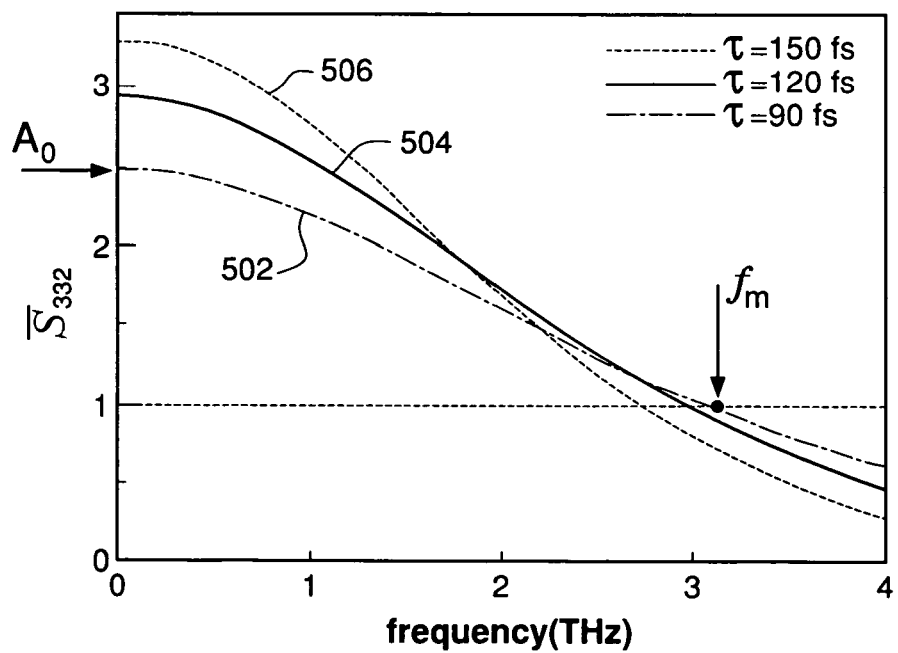
FIG. 5 graphically illustrates the sensitivity of the detection subsystem of the imaging system of FIG. 1 as a function of frequency of the THz radiation field for the embodiment of that subsystem corresponding to FIG. 4.

FIG. 5 graphically illustrates the sensitivity of detection subsystem 130 as a function of frequency of THz radiation for the embodiment of that subsystem corresponding to FIG. 4. More specifically, the vertical axis labeled $\bar{S}_{332}$ in FIG. 5 represents the magnitude of signal 332 produced by detection subsystem 130 having EO probe 200 divided by the magnitude of signal 332 that would be produced by detection subsystem 130 having a conventional (i.e., non-resonating) EO probe that is comparable in size to EO probe 200. As such, the values of $\bar{S}_{332}$ that are greater than one represent a sensitivity enhancement for detection subsystem 130, which is associated with the use of EO probe 200. Similarly, the values of $\bar{S}_{332}$ that are smaller than one represent a sensitivity loss for detection subsystem 130 equipped with EO probe 200. The break-even frequency, i.e., the frequency at which $\bar{S}_{332}=1$, is hereafter labeled as $f_m$.

Three curves 502-506 shown in FIG. 5 correspond to three different configurations of detection subsystem 130 that utilize pump-pulse durations of 90, 120, and 150 fs, respectively. Frequency $f_m$ is indicated by the vertical arrow for one of these curves, i.e., curve 502. The data of FIG. 5 indicate that the use of EO probe 200 in detection subsystem 130 generally provides a sensitivity enhancement in the frequency range below about 3 THz. A maximum sensitivity enhancement is generally reached at low frequencies and is hereafter labeled as $A_0$. For example, as indicated in FIG. 5, for curve 502, $A_0 \approx 2.5$.

Figure 6:
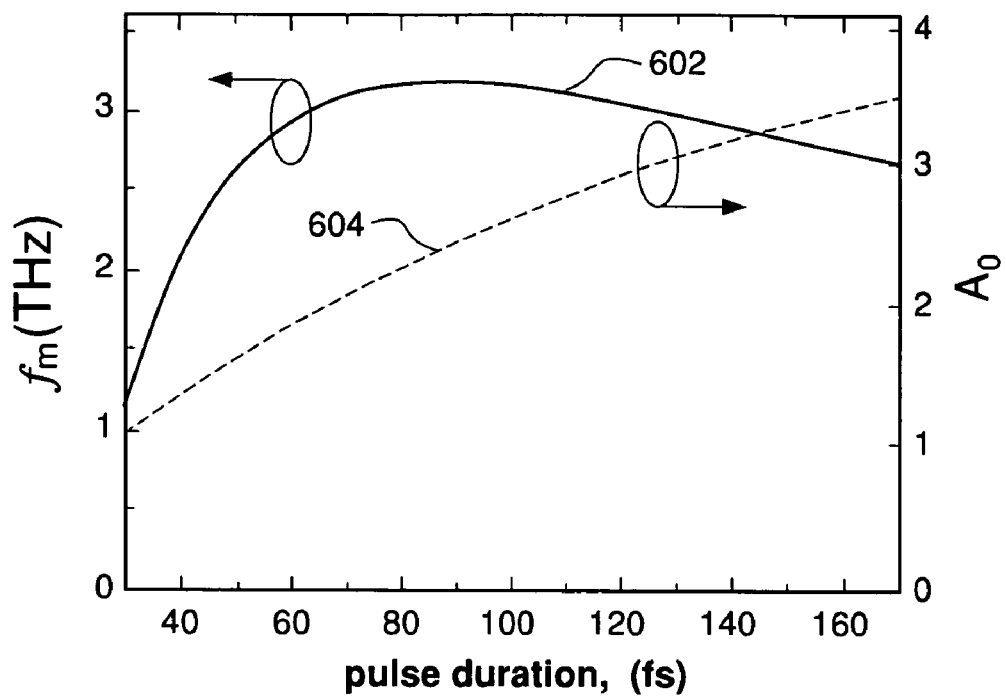
FIG. 6 graphically shows break-even frequency $f_m$ and maximum sensitivity enhancement $A_0$ in the detection subsystem of the imaging system of FIG. 1 as functions of the pump-pulse duration for the embodiment of that subsystem corresponding to FIG. 4.

FIG. 6 shows break-even frequency $f_m$ and maximum sensitivity enhancement $A_0$ in the detection subsystem 130 as functions of the pump-pulse duration for the embodiment of that subsystem corresponding to FIG. 4. More specifically, curve 602 represents $f_m$, and curve 604 represents $A_0$. The data of FIG. 6 indicate that it might be beneficial for detection subsystem 130 to employ pump pulses that have a duration of about 50 fs or longer. One reason for the values of $f_m$ and $A_0$ to decrease when relatively short pump pulses are employed is that the relatively short pulses have a relatively broad spectral width. Since the electro-optic effect in the resonator of EO probe 200 is enhanced only in the spectral region that is sufficiently close to the resonant wavelength $\lambda_0$ of the resonator, the relatively broad spectral width causes these pump pulses to acquire a reduced phase shift compared to that of relatively long (e.g., longer than 50 fs) pulses that have a spectral width that better matches the bandwidth of the resonator. In addition, the reflectivity of reflector 220 in EO probe 200 is generally higher for the shorter pulses, which attenuates the pump-light intensity in the resonator's cavity accordingly. For example, the total reflectivity of EO probe 200 in the embodiment of detection subsystem 130 illustrated by FIGS. 4-6 is 95.5 and 97% for pulse durations of 120 and 60 fs, respectively.

Figure 7:
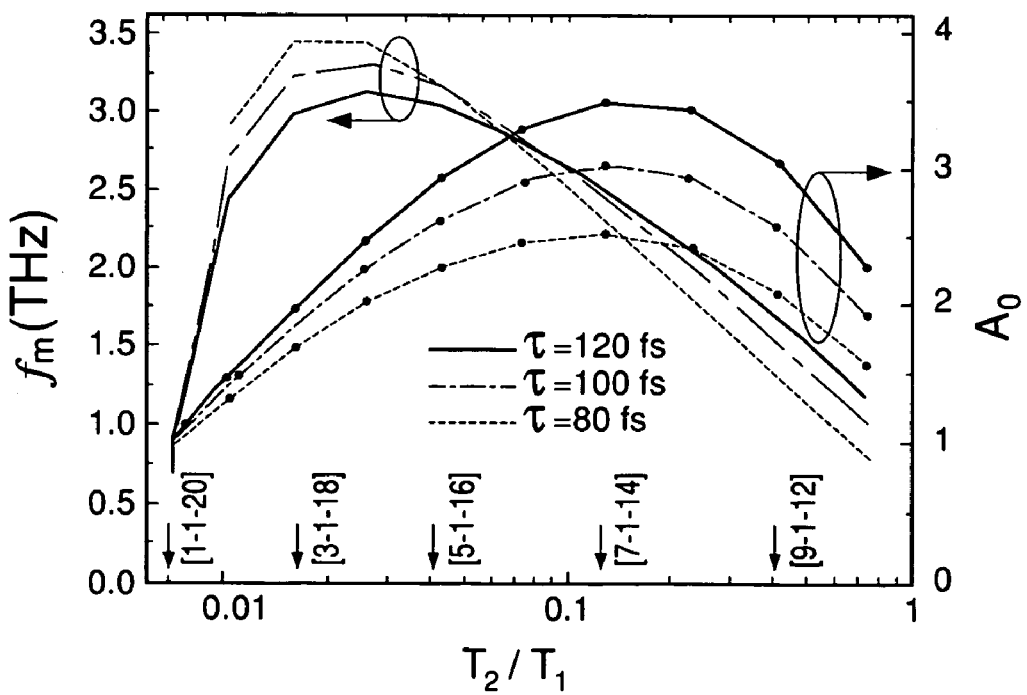
FIG. 7 graphically illustrates the dependence of break-even frequency $f_m$ and maximum sensitivity enhancement $A_0$ in the detection subsystem of the imaging system of FIG. 1 that employs the EO probe of FIG. 2 on the parameters of that probe.

FIG. 7 illustrates the dependence of break-even frequency $f_m$ and maximum sensitivity enhancement $A_0$ in detection subsystem 130 that employs EO probe 200, on the parameters of that probe. More specifically, the various implementations of EO probe 200 presented in FIG. 7 have optical resonator 216 having a thickness of about 22 half-wavelengths of the pump light in the material(s) of the optical resonator, of which thickness about 21 half-wavelengths are attributed to the combined thickness of reflectors 220 and 222, and the remaining one half-wavelength is attributed to EORM layer 224. In other words, reflectors 220 and 222 have a total of 21 quarter-wavelength layer pairs 230/232, with the various implementations presented in FIG. 7 differing only in the number of those quarter-wavelength layer pairs belonging to reflectors 220 and 222, respectively. In FIG. 7, these various implementations of EO probe 200 are designated by labels having the format of [N-1-M], in which format N and M represent the numbers of quarter-wavelength layer pairs 230/232 in reflectors 222 and 220, respectively, and the figure "1" between N and M represents the constant one half-wavelength thickness of EORM layer 224. For example, the embodiment of EO probe 200 designated in FIG. 7 as [5-1-16] has five quarter-wavelength layer pairs 230/232 in reflector 222 and sixteen such pairs in reflector 220. Note also that the value of N+M+1 in FIG. 7 is always 22, which signifies the fact that all data in the figure correspond to implementations of optical resonator 216 having a thickness of twenty-two half-wavelengths of the pump light. Since the reflectivity of each of reflectors 220 and 222 depends on the number of quarter-wavelength layer pairs 230/232 in the reflector, it is convenient to quantify the various implementations of EO probe 200 presented in FIG. 7 using the value of $T_2/T_1$, where $T_1$ and $T_2$ are the reflection coefficients of reflectors 220 and 222, respectively. Accordingly, the horizontal axis in FIG. 7 represents (in a logarithmic scale) the value of $T_2/T_1$, with the various vertical arrows along the horizontal axis indicating the values of $T_2/T_1$ for their respectively labeled [N-1-M] resonator implementations. Both break-even frequency $f_m$ and maximum sensitivity enhancement $A_0$ are shown in FIG. 7 for three different values of the pump-pulse duration, i.e., 80, 100, and 120 fs.

The data of FIG. 7 indicate that, for each Of $f_m$ and $A_0$, there is an optimum range of $T_2/T_1$. For example, for break-even frequency $f_m$, the optimum range of $T_2/T_1$ is between about 0.01 and 0.3. Similarly, for maximum sensitivity enhancement $A_0$, the optimum range of $T_2/T_1$ is between about 0.04 and 0.7. If a simultaneous optimization of both $f_m$ and $A_0$ is desirable, then EO probe 200 can be implemented to have a value of $T_2/T_1$ between about 0.03 and 0.2.

The results of FIG. 7 can qualitatively be explained as follows. When input reflector 220 has a relatively low reflection coefficient (which corresponds to a relatively large value of $T_2/T_1$, e.g., about one), the input reflector admits a large portion of the pump pulse into the resonator's cavity. As already mentioned above, the reflected waveform contains two peaks (FIG. 4A). However, only the second peak carries the electro-optic phase shift originating in EORM layer 224, and the distribution of energy between the two peaks depends on the value of $T_2/T_1$. In addition, a resonator with a $T_2/T_1$ value that is close to one has a Q-factor of about 400-500, where the Q-factor is defined as an average number of round trips in the resonator's cavity that a photon performs before escaping the cavity. Having a Q-factor this high causes the resonator to have a relatively slow response. In the other limiting case of $T_2/T_1 \ll 1$, the Q factor is reduced to about 50 and, consequently, the magnitude of the EO effect becomes small due to a relatively low number of round trips. As a result, an optimum electro-optic enhancement and fast response can be achieved in a resonator having a value of $T_{2/T1}$ somewhere between about 0.01 and 1, which is clearly indicated in FIG. 7 by the presence of the respective maxima in the curves representing of $f_m$ and $A_0$.

The data presented in FIGS. 4-7 provide guidance for appropriately designing and configuring detection subsystem 130 for near-field T-ray imaging. Advantageously, detection subsystem 130 can be designed and configured for efficient near-field detection of THz radiation in the frequency range up to about 3 THz. Since reflector 222 has a relatively small thickness, e.g., on the order of 1 µm, the THz field intensity can be probed as close to the sample surface as about 1 µm. Since EORM layer 224 has a thickness of less than 1 µm, the spatial resolution in the direction normal to the sample surface can be better than about 1 µm. The lateral spatial resolution (i.e., the spatial resolution within a plane that is parallel to the sample surface) in detection subsystem 130 is generally limited by the size of the focused pump beam, which, in principle, can be as small as about the wavelength of the pump light. Thus, for detection subsystem 130 configured to use pump light having a wavelength of about 1 µm, the lateral spatial resolution can be as good as about 1 µm. The THz-field-induced EO phase shift in EO probe 200 having a GaAs EORM layer 224 can be as high as about $10^{-6}$ radian at THz-field strengths of about 10 V/cm. Since relatively bright THz radiation sources capable of producing THz-field strengths of about 100 V/cm have become available, the use of one of such sources in system 100 can produce phase shifts as high as about $10^{-5}$ radian. Unlike a conventional near-field THz imaging system, certain embodiments of system 100 can advantageously have a fully optical scan capability, where only the optical pump beam moves over the sample, while the EO probe and the sample remain stationary.

While this invention has been described with reference to illustrative embodiments, this description is not intended to be construed in a limiting sense. For example, EO probe 200 can be designed for pump light having a wavelength other than 980 nm, and detection subsystem 130 can be configured to provide that pump light and detect the pump light reflected from the probe. In general, the terms "light" and "optical" as used in this specification refer to any suitable electromagnetic radiation including, but not limited to, UV, visible, and infrared light. Although embodiments of the present invention have been described in reference to THz radiation, which interrogates the sample and is used to form the sample's image, one skilled in the art will appreciate that an imaging system that is analogous to system 100 can similarly be designed for any other suitable interrogation radiation. Various modifications of the described embodiments, as well as other embodiments of the invention, which are apparent to persons skilled in the art to which the invention pertains are deemed to lie within the principle and scope of the invention as expressed in the following claims.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments mutually exclusive of other embodiments. The same applies to the term "implementation."

Unless explicitly stated otherwise, each numerical value and range should be interpreted as being approximate as if the word "about" or "approximately" preceded the value of the value or range.

It will be further understood that various changes in the details, materials, and arrangements of the parts which have been described and illustrated in order to explain the nature of this invention may be made by those skilled in the art without departing from the scope of the invention as expressed in the following claims.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the present invention.

Although the elements in the following method claims, if any, are recited in a particular sequence with corresponding labeling, unless the claim recitations otherwise imply a particular sequence for implementing some or all of those elements, those elements are not necessarily intended to be limited to being implemented in that particular sequence.

What is claimed is:

1. A method of detecting interrogation radiation, comprising:
    pumping an optical resonator having an electro-optically responsive material (EORM) with pump light, wherein the pump light traverses the EORM; and
    detecting at least a portion of the pump light output from the resonator, while exposing the EORM to the interrogation radiation, wherein:
        the optical resonator is defined by first and second reflectors, wherein the EORM is interposed between said first and second reflectors; and
        one of the first and second reflectors comprises a Bragg reflector.

2. The invention of claim 1, wherein the interrogation radiation comprises THz radiation.

3. The invention of claim 1, further comprising:
positioning the EORM in near-field proximity to a surface of a sample; and
repeating the steps of pumping and detecting such that, for at least some repetitions, the pump light traverses the EORM at different spatial locations with respect to said surface.

4. The invention of claim 3, further comprising forming an image of the sample based on the detection results.

5. The invention of claim 3, comprising the step of scanning a beam of the pump light over the resonator while keeping position of the resonator with respect to the sample substantially unchanged.

6. The invention of claim 3, comprising the step of changing relative position of the resonator and the sample.

7. The invention of claim 1, wherein:
pumping the optical resonator comprises the step of transmitting the pump light from outside the resonator through the first reflector and into the resonator interior.

8. The invention of claim 7, further comprising:
reverberating the pump light between the first and second reflectors; and
transmitting the pump light from the resonator interior through the first reflector.

9. The invention of claim 7, wherein each of the first and second reflectors is a Bragg reflector.

10. The invention of claim 1, wherein:
the EORM is characterized by first and second principal polarization axes; and
the step of detecting comprises:
constructively interfering pump light polarized along the first and second principal polarization axes to form a first output beam;
destructively interfering the pump light polarized along the first and second principal polarization axes to form a second output beam; and
converting the first and second output beams into an electrical signal indicative of a phase shift between the pump light polarized along the first principal polarization axis and the pump light polarized along the second principal polarization axis.

11. The invention of claim 10, wherein the step of detecting comprises introducing a constant $\pi/2$ phase shift between the pump light polarized along the first principal polarization axis and the pump light polarized along the second principal polarization axis.

12. A system, comprising:
an optical resonator having an electro-optically responsive material (EORM), wherein said resonator is adapted to be pumped with pump light such that the pump light traverses the EORM, wherein the EORM is adapted to be exposed to interrogation radiation; and
an optical detector adapted to detect at least a portion of the pump light output from the resonator having the EORM exposed to the interrogation radiation, wherein:
the optical resonator is defined by first and second reflectors, wherein the EORM is interposed between said first and second reflectors; and
one of the first and second reflectors comprises a Bragg reflector.

13. The invention of claim 12, wherein the interrogation radiation comprises THz radiation.

14. The invention of claim 12, wherein:
the EORM is adapted to be positioned in near-field proximity to a surface of a sample; and
the system is adapted to form an image of the sample by configuring the detector to serially detect the pump light that traversed the EORM at two or more different spatial locations with respect to said surface.

15. The invention of claim 14, wherein the system is adapted to scan a beam of the pump light over the resonator, while keeping position of the resonator with respect to the sample substantially unchanged.

16. The invention of claim 12, wherein:
each of the first and second reflectors is a Bragg reflector.

17. The invention of claim 12, wherein, for the pump light, a ratio of the reflection coefficient of the second reflector to the reflection coefficient of the first reflector has a value between about 0.01 and 0.7.

18. The invention of claim 12, further comprising:
a first source adapted to produce the interrogation radiation; and
a second source adapted to produce the pump light, wherein the system is adapted to function using at least one of pulsed pump light and pulsed interrogation radiation.

19. The invention of claim 12, wherein:
the EORM is characterized by first and second principal polarization axes; and
the detector comprises:
a polarizing beam splitter adapted to: (i) constructively interfere pump light polarized along the first and second principal polarization axes to form a first output beam and (ii) destructively interfere the pump light polarized along the first and second principal polarization axes to form a second output beam; and
a balanced photodetector pair adapted to convert the first and second output beams into an electrical signal indicative of a phase shift between the pump light polarized along the first principal polarization axis and the pump light polarized along the second principal polarization axis.

20. The invention of claim 19, wherein the detector comprises a quarter-wave plate adapted to introduce a constant $\pi/2$ phase shift between the pump light polarized along the first principal polarization axis and the pump light polarized along the second principal polarization axis.

21. A method of detecting interrogation radiation, comprising:
pumping an optical resonator having an electro-optically responsive material (EORM) with pump light, wherein the pump light traverses the EORM;
positioning the EORM in near-field proximity to a surface of a sample; and
detecting at least a portion of the pump light output from the resonator, while exposing the EORM to the interrogation radiation.

22. The invention of claim 21, wherein the interrogation radiation comprises THz radiation.

* * * * *

UNITED STATES PATENT AND TRADEMARK OFFICE
CERTIFICATE OF CORRECTION

PATENT NO. : 7,608,827 B2
APPLICATION NO. : 11/350992
DATED : October 27, 2009
INVENTOR(S) : Oleg Mitrofanov It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 647 days.

Signed and Sealed this

Twelfth Day of October, 2010

David J. Kappos
*Director of the United States Patent and Trademark Office*